United States Patent [19]

Jung et al.

[11] Patent Number: 5,233,069
[45] Date of Patent: Aug. 3, 1993

[54] BIS(SILYL)METHANES AND THEIR DIRECT SYNTHESIS

[75] Inventors: Il N. Jung, Seoul; Seung H. Yeon, Kyungki-Do; Joon S. Han, Seoul, all of Rep. of Korea

[73] Assignee: Korea Institute of Science and Technology, Seoul, Rep. of Korea

[21] Appl. No.: 965,705

[22] Filed: Oct. 23, 1992

[30] Foreign Application Priority Data

Dec. 24, 1991 [KR] Rep. of Korea ............... 24243/1991

[51] Int. Cl.$^5$ .............................................. C07F 7/08
[52] U.S. Cl. .................................................. 556/435
[58] Field of Search ......................................... 556/435

[56] References Cited

U.S. PATENT DOCUMENTS 5,075,477 12/1991 Jung et al. ........................ 556/435

Primary Examiner—Paul F. Shaver
Attorney, Agent, or Firm—Birch, Stewart, Kolasch & Birch

[57] ABSTRACT

The present invention relates to bis(silyl)methanes and their preparation methods in high hields by directly reacting α-chloromethylsilanes represented by formula I incorporated with hydrogen chloride or alkylchlorides represented by the general formula II, with silicon metal to give the bis(silyl)methane compound having dichlorosily group (formula III) as the major products and the bis(silyl)methane compounds having trichlorosilyl group (formula IV) in moderately high yields in the presence of copper catalyst at a temperature from 250° C. to 350° C. The different major product is obtained depending upon the chloride incorporated. n-Butyl chloride, t-butyl chloride, propyl chloride, and hydrogen chloride gave bissilylmethane with hydrogen substituted on the silicon atom as the major product. When 1,2-dichloroethane is incorporated, bis(-silyl)methanes having trichlorosilyl group is the major product.

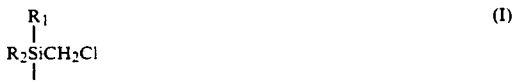

(I)

RCl (II)

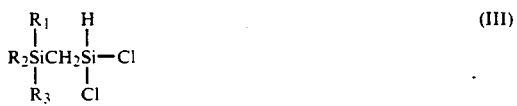

(III)

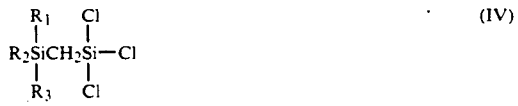

(IV)

In formulae (I), (III), (IV), $R_1$, $R_2$, and $R_3$ are independently methyl group or chlorine atome; and R is hydrogen, alkyl($C_1$–$C_4$), $CH_2CH_2Cl$.

18 Claims, No Drawings

BIS(SILYL)METHANES AND THEIR DIRECT SYNTHESIS

BACKGROUND OF THE INVENTION

1. Field of the Invention

The present invention relates to bis(silyl)methanes and a process for preparing the same by directly reacting α-chloromethylsilanes represented by the general formula I incorporated with hydrogen chloride or alkylchlorides represented by the general formula II, with silicon metal to give the bis(silyl)methane compound having dichlorosily group (formula III) as the major products and the bis(silyl)methane compounds having trichlorosilyl group(formula IV) in moderately high yields in the presence of copper catalyst at a temperature from 250° C. to 350° C. The preferred reaction temperature range is 300°–330° C. Useful copper catalysts include copper metal, copper salts, and partially oxidized copper.

(I)

In formula I, $R_1$, $R_2$, and $R_3$ are independently methyl group or chlorine atom.

RCl     (II)

In formula II, R is hydrogen, alkyl ($C_1$–$C_4$), $CH_2CH_2Cl$.

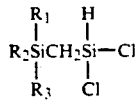
(III)

In formula III, $R_1$, $R_2$, and $R_3$ are independently methyl group or chlorine atom.

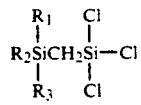
(IV)

In formula IV, $R_1$, $R_2$, and $R_3$ are independently methyl group or chlorine atom.

2. Description of the Prior Art

Trichlorosilane is a very important starting material for semiconductor grade silicon and also for silicones, because it undergoes hydrosilylation reaction to the unsaturated organic compounds. Trichlorosilane is commercially manufactured by the direct reaction of elemental silicon with hydrogen chloride in the presence of copper catalyst (A. D. Petrov, B. E. Mironov, V. A. Ponomaren Ko, and E. A. Chernyshev, "Synthesis of Organosilicon Monomers" Consultants Bureau, New York, 1964). The reaction is carried out at 200°–500° C. and gives trichlorisalane as the major product and tetrachlorosilane, hydrogen, and dichlorosilane as the minor products. The reaction conditions such as the nature of the starting materials, the catalyst, the reaction temperature, the reaction pressure, the type of reactor used etc. should be optimized to get the maximum yield of trichlorosilane.

$Si + HCl \rightarrow HSiCl_3 + SiCl_4 + H_2$

Methyldichlorosilane which has methyl group and hydrogen on silicon is frequently used in the manufacture of modified silicone fluids and room temperature vulcanizing silicone rubbers. Methyldichlorosilane is obtained in about 3% yield as a by-product from the direct reaction of elemental silicon with methyl chloride (R. J. H. Voorhoeve, Organohalosilanes: Precursors to silicones, Elsevier Publishing Company, New York, 1967).

$Si + CH_3Cl \rightarrow (CH_3)_2SiCl_2 + CH_3HSiCl_2(-3\%)$

Yamada reported that methyldichlorosilane could be prepared in higher yields by reacting elemental silicon with the mixed gases of methyl chloride and hydrogen chloride (S. Yamada and E. Yasunaga, Japanese Patent 6162(1952). Halm also reported that methyldichlorosilane could be obtained up to 9.5% yield by adding 15% of hydrogen chloride to methyl chloride in the direct synthesis of methylchlorosilanes (R. L. Halm and R. H. Zapp, U.S. Pat. No. 4,966,986).

In 1953, Petrov and his co-workers reported that the yield of alkyldichlorosilane increased in the direct reaction of elemental silicon with alkyl chloride as the bulkiness of the alkyl group increased. They obtained 30% yield of butyldichlorosilane from the reaction of elemental silicon with butyl chloride (A. D. Petrov, N. P. Smetankina and G. I. Nikishin, Zh. Obshch, Khim, 25, 2332 (1953), CA 50-9280). This was explained by that butyl chloride decomposed to give off hydrogen chloride and the mixed gases of butyl chloride and hydrogen chloride reacted with elemental silicon to give butyldichlorosilane.

$Si + BuCl \rightarrow BuHSiCl_2$

Fritz and his co-worker first reported that Si-H containing bis (trichlorosilyl) (dichlorosilyl)methane was obtained in about 3% as a byproduct from the direct reaction of elemental silicon with methylene chloride in the presence of copper catalyst at 280° C. (G. Fritz and H. Thielking, Z. Anorg. u. Allgem. Chem., 306,39 (1960). In this case, the yield was not very high and the decomposition of methylene chloride easily deactivated the elemental silicon and copper catalyst and made the process economically less feasible.

In 1957, Dannels and Post reported that bis(trimethylsilyl) (dichlorosilyl)methane was prepared by reacting trimethylsilylmethylmagnesium bromide with trichlorosilane in 64% yield (B. F. Dannels and H. W. Post, J. Org. Chem., 22, 748 (1957). However, the Grignard reagent costs high and the process requires handling of highly flammable ether solvent. This make the process economically less feasible.

In 1974, Sommer and his co-workers reported that bis (dimethylchlorosilyl) (dichlorosilyl)methane was obtained in 22% yield from the co-pyrolysis of dimethylsilacyclobutane with trichlorosilane at 611° C. The starting cyclic compound was again prepared by Grignard method.

We also reported that the trisilaalkanes represented by the general formula V as the major products and bissilylmethanes represented by the general formula IV as the minor products were prepared by reacting α-chloromethylsilanes represented by the general formula I with elemental silicon in the presence of copper catalyst at a temperature from 250°-350° C. The copper catalyst was used 1-20% of total contact mixture, but the preferred amount was 5-10%. The reaction could be carried out in a fluidized bed or in a stirred bed reactor. Addition of microspherical acid clay to silicon metal improved the fluidization and gave better results (I.N. Jung, G. H. Lee, S. H. Yeon, M. Suk, U.S. patent application, Ser. No. 07/697,165 (May 8, 1991).

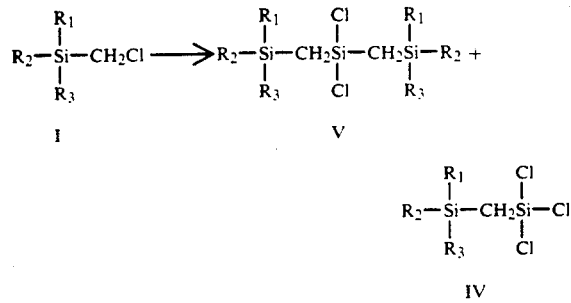

wherein $R_1$, $R_2$, and $R_3$ represent independently chlorine atom or methyl group.

SUMMARY OF THE INVENTION

It is an object of the invention to provide bis(sily)methanes which can be used as an important starting material for preparing silicone compounds having various organic functional groups.

Another object of the invention is to provide a direct synthetic method for the preparation of bis(silyl)methanes. These objects of the present invention will become more apparent in the detailed description and examples which follow.

DETAILED DESCRIPTION OF THE INVENTION

The present invention relates to a process for preparing bis(silyl) methanes by directly reacting α-chloromethylsilanes represented by the general formula I which is incorporated with hydrogen chloride or alkylchlorides represented by the general formula II such as propyl chloride, butyl chloride, and 1,2-dichloroethane, with silicon metal to give the bis(silyl)methane compound having dichlorosily group represented by the general formula III as the major products and the bis(silyl)methane compounds having trichlorosilyl group represented by the general formula IV in moderately high yields in the presence of copper catalyst at a temperature from 250° C. to 350° C. The preferred reaction temperature range is 300°-330° C. Useful copper catalysts include copper metal, copper salts, partially oxidized copper.

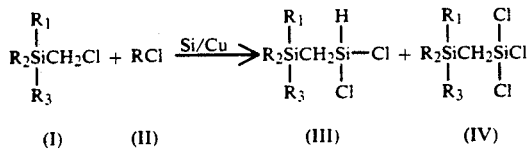

In formula I-IV, $R_1$, $R_2$, and $R_3$ are independently methyl group or chlorine atom and R can be hydrogen; alkyl($C_1$-$C_4$), or $CH_2CH_2Cl$.

The reactants of formulae I and II are blended before they are introduced to the reactor. They can be mixed in gaseous state after they are vaporized, or also in liquid state when formula II compound is liquid. The blending ratio of the compound II to each mole of the compound I can be from 0.1-4.0 moles, but the preferred ratio is 1.0-3.0 moles.

The reaction can be carried out in a fluid bed or in a stirred bed reactor. In the fluidized bed reaction, the addition of inert nitrogen gas to the starting gases is recommended to improve the fluidization. This also helps to remove the high boiling-point products out of the reactor. The pressure at which the reaction of the present invention is conducted is not critical and may be varied from 1 to 5 atmospheres, preferably 1 to 3 atmospheres.

Metallurgical grade silicon was employed in the process of this invention, which contained more than 95% silicon by weight. The preferred purity of silicon was higher than 98%. The particle size of the silicon was 1-200 micron, but 20-200 micron was used for the fluidized reaction. The reaction temperature was from 250° C. to 350° C. The preferred reaction temperature range was 280°-320° C. The reaction pressure was from 1 to 5 atmospheres. Addition of micro-spherical acid clay to silicon metal improved the fluidization and gave better results.

The commercially available copper catalysts for the reaction between silicon and methyl chloride are also found to be good for these reactions. The content of copper catalyst is 1-20% of total contact mass. The preferred copper content is 5-10%. The process of the present invention is characterized to include promotors. The range of the promotors content is 0.001-5.0%. The promotors include calcium, barium, zinc, tin, cadmium, manganese, magnesium, silver, chromium, but are not limited to them.

The invention will be further illustrated by the following examples. It is, however, not intended that this invention will be limited by the examples.

EXAMPLE 1

Preparation of Si/Cu contact mixture (I)

360 g (325-60 mesh) of silicon is mixed with 62.3 g of CuCl (10% of copper based on the weight of the silicon and copper) as a catalyst to provide a mixture, then the mixture is fed to the reactor. Thereafter, the mixture was heated to a temperature ranging from 180° C. to 250° C. At this time, the agitator is operated at 60 rpm. In order to mix the mixture completely together with blowing slowly dried nitrogen. When the temperature in the reactor is raised to about 370° C., the silicon is reacted with the CuCl to form η-phase $Cu_3Si$, and $SiCl_4$ is obtained as a by-product which is removed from the reactor. In the case of using a promotor, 0.8 g of a promotor metal is added to the mixture after the reaction is completed.

EXAMPLE 2

Preparation of Si/Cu Contact Mixture (II)

In case of using metallic copper or copper catalysts instead of the CuCl in the synthesis of methylchlorosilanes as described in EXAMPLE 1, 10% of the copper based on the weight of the silicon and copper was mixed with the silicon. The mixture was heated to the temperature of 350° C. for 2 hours in the reactor together with blowing hydrogen chloride or methyl chloride in order to activate the same.

The composition of the contact mixtures prepared in Example 1 and 2 is shown in Table 1.

TABLE 1

| Sample No. | Si (g) | Cu Catalyst Form | (g) | Promotor Metal | (g) | Metal | (g) | Remark |
|---|---|---|---|---|---|---|---|---|
| I-1 | 360 | CuCl | 62.3 | | | | | |
| I-2 | 380 | Cu | 20.0 | | | | | |
| I-3 | 360 | CuC | 40.0 | Cd | 2.0 | | | |
| I-4 | 360 | Cu | 40.0 | Zn | 2.0 | | | |
| I-5 | 380 | Cu | 20.0 | Cd | 2.0 | Sn | 0.02 | |
| I-6 | 380 | Cu | 20.0 | Ca | 2.0 | | | |
| I-7 | 380 | Cu | 20.0 | Ca | 2.0 | Cd | 2.0 | |
| I-8 | 360 | Cu | 40.0 | Ag | 2.0 | | | |
| I-9 | 360 | Cu | 40.0 | Ag | 2.0 | Cd | 2.0 | |
| I-10 | 360 | Cu | 40.0 | Mn | 2.0 | | | |
| I-11 | 360 | Cu | 40.0 | Mn | 2.0 | Cd | 2.0 | |
| I-12 | 360 | Cu | 40.0 | Mg | 2.0 | | | |
| I-13 | 360 | Cu | 40.0 | Mg | 2.0 | Cd | 2.0 | |
| I-14 | 360 | Cu | 40.0 | Cr | 2.0 | | | |
| I-15 | 360 | Cu | 40.0 | Cr | 2.0 | Cd | 2.0 | |

EXAMPLE 3

Reaction of Silicon and the 1:3 Mixture of Chloromethyldimethylchlorosilane and Hydrogen Chloride 402 g of Si/Cu contact mixture (I-3) obtained from silicon and CuCl was charged in an agitating-type reaction bath, and 250 g of chloromethyldimethylchlorosilane was charged in a syringe pump. After increasing the temperature in the reactor up to 320° C., the silane was pumped at the rate of 0.6 ml/min to the evaporator attached to the bottom of the reactor, while $N_2$ and hydrogen chloride were also blown thereto at the rate of 240 ml/min and 300 ml/min respectively. 5 minutes after the initiation of pumping, increasing of the temperature caused by an exothermic nature of the reaction was observed and reaction products began to flow along the wall of an receiver flask. While maintaining the above conditions, reaction product was taken every hour. After the reaction for 6 hours, 333.9 g of products was collected, while 234.8 g of the silane was used.

The obtained reaction products were analyzed by using a gas chromatography (capillary column, SE-54, 12 m, or packed column, SE-30, 4.25 m×⅛" OD.SS) and fractionally distilled to separate its constituents from one another, so that their structures could be determined. The structure of each constituent was determined by using an infrared spectroscopy, a nuclear magnetic resonance spectroscopy and a mass spectroscopy.

The products contained 195.3 g (58.5%) of 1,1,3-trichloro-3-methyl-1,3-disilabutanel[b.p. 155°–157° C.; NMR ($CDCl_3$), 5.66 (t, 1H, Si-H), 1.00 (d, 2H, $-CH_2-$), 0.60 (s, 6H, $-CH_3-$)]and 48.1 g (14.4%) of 1,1,1,3-tetrachloro-3-methyl-1,3-disilabutane [b.p. 169.5°–170° C.; NMR 1.30 ppm (s, 2H, $CH_2$), 0.66 ppm (s, 6H, $CH_3$)]. 27.1% of by product contained 3.0% of trimethylchlorosilane, 8.7% of trichlorosilane, 8.8% of the starting silane and about 6% of the balance was unidentified substances.

The reaction was carried out under the same condition and by the same reactor as employed above, except that the reaction temperature varied from 280° C. to 340° C. The results obtained from the reactions are shown in Table 2.

TABLE 2

Reaction Temperatures and Products

| Exp. No. | React. Temp. (°C.) | Silane (g) | React. Time (hr) | Amt. of products (g) | compd. of formula III | compd. of formula IV | others | starting silane |
|---|---|---|---|---|---|---|---|---|
| 1 | 280 | 234.8 | 6.0 | 308.0 | 46.9 | 12.5 | 12.5 | 19.0 |
| 2 | 300 | 234.8 | 6.0 | 314.6 | 55.3 | 14.5 | 14.5 | 6.3 |
| 3 | 320 | 234.8 | 6.0 | 333.9 | 58.5 | 14.4 | 14.4 | 8.8 |
| 4 | 340 | 234.8 | 6.0 | 315.9 | 48.8 | 20.5 | 20.5 | 4.8 |

EXAMPLE 4

Reaction of Silicon and the Mixtures of Chloromethyldimethylchlorosilane and Hydrogen Chloride The reaction was carried out under the same condition and by the same reactor as employed in Exp. No. 3, except that the mixing ratio of the silane and hydrogen chloride varied from 1:1.2 to 1:4. The results obtained from the reactions are shown in Table 3. The results shown in Exp. No. 8 of Table 3 are obtained from the reaction in which 20.0 g (5% based on the weight of the silicon and copper) of acid clay was added to the contact mixture.

TABLE 3

The mixing ratio of Reactants and Products

| Exp. No. | Silane (g) | React. Time (hr) | Ratio of silane: CHl (mole) | Amt. of products (g) | compd. of formula III | compd. of formula IV | others | starting silane |
|---|---|---|---|---|---|---|---|---|
| 5 | 156.4 | 4.0 | 1:1.2 | 161.6 | 31.7 | 29.5 | 33.2 | 56 |
| 6 | 156.4 | 4.0 | 1:2.5 | 192.4 | 48.4 | 19.9 | 27.3 | 4.4 |
| 7 | 156.4 | 4.0 | 1:4 | 225.6 | 63.5 | 13.6 | 15.2 | 7.7 |
| 8 | 156.4 | 4.0 | 1:3 | 207.3 | 59.3 | 13.2 | 18.6 | 8.9 acid clay |

EXAMPLE 5

Reaction of Silicon and the 1:3 Mixtures of Chloromethyldimethylchlorosilane and Hydrogen Chloride The reaction was carried out under the same condition and by the same reactor as employed in Exp. No. 3 of Example 3, except the different contact mixture was used. All the contact mixture listed in Table 1 have been tested and the results obtained from the reactions are shown in Table 4.

TABLE 4

| | | | | | Contact Mixtures and Products | | | |
| | | | | | Composition ratio of products (%) | | | |
| Exp. No. | contact mixture(g) | Silane (g) | React. Time (hr) | Amt. of products (g) | compd. of formula III | compd. of formula IV | others | starting silane |
|---|---|---|---|---|---|---|---|---|
| 9 | I-1 | 117.4 | 3.0 | 163.8 | 11.9 | 32.2 | 45.0 | 10.9 |
| 10 | I-2 | 117.4 | 8.0 | 154.2 | 33.0 | 28.9 | 25.5 | 14.8 |
| 11 | I-4 | 163.0 | 4.0 | 249.0 | 15.5 | 8.9 | 44.0 | 31.6 |
| 12 | I-5 | 117.4 | 3.0 | 166.5 | 20.0 | 46.6 | 24.2 | 8.4 |
| 13 | I-6 | 117.4 | 3.0 | 210.4 | 4.0 | 33.5 | 61.4 | 1.1 |
| 14 | I-7 | 117.4 | 3.0 | 213.8 | 15.9 | 24.8 | 58.1 | 1.2 |
| 15 | I-8 | 140.0 | 3.5 | 257.2 | 16.5 | 54.7 | 27.3 | 1.5 |
| 16 | I-9 | 117.4 | 3.0 | 202.9 | 42.9 | 25.6 | 29.7 | 1.8 |
| 17 | I-10 | 140.0 | 3.5 | 226.2 | 18.6 | 43.1 | 37.4 | 0.9 |
| 18 | I-11 | 117.4 | 3.0 | 207.4 | 44.2 | 29.7 | 25.2 | 0.9 |
| 19 | I-12 | 140.0 | 3.5 | 238.0 | 14.7 | 52.7 | 30.5 | 2.1 |
| 20 | I-13 | 117.4 | 3.0 | 215.7 | 33.8 | 26.3 | 37.4 | 2.5 |
| 21 | I-14 | 140.0 | 3.5 | 245.6 | 10.5 | 43.6 | 41.8 | 4.1 |
| 22 | I-15 | 117.4 | 3.0 | 218.8 | 47.9 | 22.9 | 27.8 | 1.4 |

EXAMPLE 6

Reaction of Silicon and the Mixtures of Chloromethyldimethylchlorosiliane and Alkyl Chlorides The following experiment demonstrates Exp. No. 25. The reaction was carried out under the same condition and by the same reactor as employed in Example 3, except that the same amount of t-butyl chloride was used instead of hydrogen chloride. After the reaction for 4 hours, 268.6 g of products was collected, while 156.5 g of the silane was used. The product contained 144.5 g (53.8%) of 1,1,3-trichloro-3-methyl-1,3-disilabutane and 55.3 g (20.6%) of 1,1,1,3-tetrachloro-3-methyl-1,3-disilabutane. 25.6% of byproduct contained 3.1% of trimethylchlorosilane and 11.3% of trichlorosilane, but the starting silane was not detected. The gaseous byproduct which was not trapped in the condenser was detected to be mostly isobutene produced from the decomposition of t-butyl chloride.

The reaction was carried out under the same condition and by the same reactor as employed above, except that the mixing ratio of the silane and alkyl chloride varied and different contact mixtures were used. The results obtained from the reactions are shown in Table 5.

EXAMPLE 7

Reaction of Silicon and the Mixtures of Chloromethyldimethylchlorosilane and Alkyl Chloride Using a Fluidized Bed Reactor 402 g of Si/Cu contact mixture (I-3) obtained from silicon and CuCl was charged in a fluidized reaction bath and 225.4 g of the 1:3 mixture of chloromethyldimethylchlorosilane and t-butyl chloride was charged to a syringe pump. After increasing the temperature in the reactor up to 320° C., 225.4 g of the mixture was pumped at the rate of 2.5 g/min to the evaporator attached to the bottom of the reactor, while $N_2$ was also blown thereto at the rate of 240 ml/min. After the reaction for 1.5 hours, 139.4 g of products was collected, while 136.9 g of the silane was used. The products contained 12.5 g (9.0%) of 1,1,3-trichloro-3-methyl-1,3-disilabutane and 33.0 g (23.7%) of 1,1,1,3-tetrachloro-3-methyl-1,3-disilabutane. 38.5% of the product was the starting silane.

The reaction was carried out under the same condition and by the same reactor as employed above, except that the 1:1 mixing ratio of the reactants was used instead of 1:3. The reaction was also carried out under the same condition and by the same reactor as employed above, except that the hydrogen chloride was used instead of t-butyl chloride and the pressure of the reactor was raised to 3 Kg/cm$^2$. The results obtained from the reactions are shown in Table 6.

TABLE 5

| | | | | | | Reaction Conditions and Products | | | |
| | | Ratio of RCl: HCl (mole) | Contact mixture | | | Amt. products (g) | Composition ratio of products (%) | | |
| Ex. No | RCl II | | | Silane (g) | React. Time (hr) | | compd. of formula III | compd. of formula IV | others | starting silane |
|---|---|---|---|---|---|---|---|---|---|---|
| 23 | t-BuCl | 1:1 | I-3 | 156.5 | 4.0 | 195.5 | 28.5 | 32.7 | 38.8 | — |
| 24 | t-BuCl | 1:2 | I-3 | 176.1 | 4.5 | 247.2 | 40.6 | 23.2 | 36.2 | — |
| 25 | t-BuCl | 1:3 | I-3 | 156.5 | 4.0 | 268.6 | 53.8 | 20.6 | 25.6 | — |
| 26 | t-BuCl | 1:3 | I-2 | 136.9 | 3.5 | 236.5 | 40.3 | 22.0 | 37.7 | — |
| 27 | n-BuCl | 1:3 | I-3 | 156.5 | 4.0 | 332.3 | 40.7 | 10.6 | 48.7 | — |
| 28 | n-BuCl | 1:3 | I-2 | 195.7 | 5.0 | 414.2 | 31.3 | 21.5 | 47.2 | — |
| 29 | i-PrCl | 1:3 | I-5 | 136.9 | 3.5 | 265.8 | 40.9 | 17.0 | 39.8 | 2.3 — |

TABLE 6

Reaction Conditions of the Fluidized Bed Reaction and Products

| Ex. No | RCl II | Ratio of silane:HCl (mole) | Silane used (g) | React. Time (hr) | Amt. of products (g) | Composition ratio of products (%) compd. of formula III | compd. of formula IV | others | starting silane |
|---|---|---|---|---|---|---|---|---|---|
| 30 | n-Bu | 1:1 | 136.9 | 3.5 | 139.4 | 7.7 | 26.3 | 27.4 | 38.6 |
| 31 | n-Bu | 1:3 | 117.4 | 3.0 | 119.6 | 9.0 | 23.7 | 28.8 | 38.5 |
| 32 | H | 1:3 | 117.4 | 3.0 | 134.7 | 14.5 | 27.4 | 32.8 | 25.3 |
| 33 | H | 1:3 | 156.5 | 4.0 | 187.7 | 45.4 | 26.2 | 37.3 | 19.2 |

3 Kg/Cm$^2$

EXAMPLE 8

Reaction of Silicon and the Mixtures of Varous Chloromethylsilanes and Alkylchlorides The following experiment demonstrates Exp. No. 34. The reaction was carried out under the same condition and by the same reactor as employed in Example 6, except that the same amount of n-butyl chloride was used instead of t-butyl chloride. After the reaction for 4.6 hours, 466.4 g of products was collected, while 212.9 g of the silane and 361.6 g of n-butyl chloride were used. The products contained 126.9 g (35.1%) of 1,1,3,3-tetrachloro-1,3-disilabutane; [b.p. 166°-167° C.; NMR (CDCl$_3$), 5.73(t, 1H, Si-H), 1.33 (d, 2H, —CH$_2$—), 1.00 (s, 3H, —CH$_3$)] and 46.6 g of 1,1,1,3,3-pentachloro-1,3-disilabutane; [b.p. 181.5°-182° C.; NMR (CDCl$_3$) 1.53 (s, 2H, —CH$_2$—), 0.92 (s, 3H, —CH$_3$)] and 55.3 g (20.6%) of 1,1,1,3-tetrachloro-3-methyl-1,3-disilabutane. 51.4% of byproduct contained 16.7% of trimethylchlorosilane and 13.4% of trichlorosilane and about 21% of the balance was unidentified substances. The gaseous byproduct which was not trapped in the condenser was detected to be mostly 2-butene produced from the decomposition of n-butyl chloride.

The reaction was carried out under the same condition and by the same reactor as employed above, except that the different silanes and alkyl chlorides were used. The results obtained from the reactions are shown in Table 7.

EXAMPLE 9

Reaction of Silicon and the Mixtures of Chloromethylsilanes and 1,2-dischloroethane The following experiment demonstrates Exp. No. 42. The reaction was carried out under the same condition and by the same reactor as employed in Example 9, except that the same amount of 1,2-dichloroethane was used instead of n-butyl chloride and the mixing ration of silane and 1,2-dichloroethane was 1:1.2. After the reaction for 3.5 hours, 292.7 g of products was collected, while 184.6 g of the silane and 111.5 g of 1,2-dichloroethane were used. The products contained 16.4 g (5.6%) of 1,1,3,3,3-pentachloro-1,3-disilapropane and 207.2 g (70.8%) of 1,1,1,3,3,3-hexachloro-1,3-disilapropane. 23.6% of byproduct contained 2.0% of methyltrichlorosilane and about 22% of the balance was unidentified substances. The gaseous byproduct which was not trapped in the condenser was detected to be mostly ethylene produced from the decomposition of 1,2-dichlorosilane.

The reaction was carried out under the same condition and by the same reactor as employed above, except that the different silanes were used. The results obtained from the reactions are shown in Table 8.

TABLE 8

Results of the reaction of silicon with the mixtures of various chloromethylsilanes and 1,2-dichloroethane

| Ex. No. | Formula (I) R$_1$ | R$_2$ | R$_3$ | Silane (g) | React. Time (hr) | Products (g) | Composition ratio of products (%) Formula III | Formula IV | others | starting silane |
|---|---|---|---|---|---|---|---|---|---|---|
| 40 | Me | Me | Cl | 156.5 | 4.0 | 273.2 | 9.6 | 71.1 | 19.3 | — |
| 41 | Me | Cl | Cl | 212.9 | 4.6 | 350.7 | 7.2 | 69.7 | 23.1 | — |
| 42 | Cl | Cl | Cl | 184.6 | 3.5 | 292.7 | 5.6 | 70.8 | 24.6 | — |
| 43 | Me | Me | Me | 95.7 | 3.0 | 174.3 | 8.7 | 63.4 | 27.9 | — |

What is claimed is:

1. Bis(silyl)methane represented by the following formula

TABLE 7

The reactants and Products

| Ex. No. | Formula (I) R$_1$ | R$_2$ | R$_3$ | Silane (g) | R-Cl II | React. Time (hr) | Products (g) | Composition ratio of products (%) Formula III | Formula IV | others | starting silane |
|---|---|---|---|---|---|---|---|---|---|---|---|
| 34 | Me | Cl | Cl | 212.9 | n-Bu | 4.6 | 466.4 | 35.1 | 12.9 | 52.0 | — |
| 35 | Me | Cl | Cl | 212.9 | t-Bu | 4.6 | 479.8 | 41.4 | 19.2 | 39.4 | — |
| 36 | Cl | Cl | Cl | 253.1 | n-Bu | 4.8 | 431.9 | 31.0 | 12.5 | 56.5 | — |
| 37 | Cl | Cl | Cl | 242.6 | t-Bu | 4.6 | 413.8 | 45.4 | 19.7 | 35.6 | — |
| 38 | Me | Me | Me | 153.1 | n-Bu | 4.8 | 416.9 | 36.3 | 6.8 | 56.9 | — |
| 39 | Me | Me | Me | 146.7 | t-Bu | 4.6 | 278.0 | 44.3 | 15.8 | 39.9 | — |

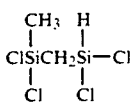

2. The method for the preparation of bis(silyl)methanes represented by the general formulae (III) and (IV), which comprises directly reacting silicon with α-chloromethylsilanes of the general formula (I) incorporated with hydrogen chloride or alkylchlorides of the general formula (II), in the presence of copper catalyst at a temperature from 250° C. to 350° C.

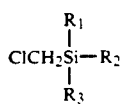 (I)

R—Cl (II)

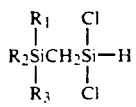 (III)

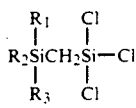 (IV)

wherein, $R_1$, $R_2$ and $R_3$ represent methyl group or chlorine atom; and R represents hydrogen, propyl, n-butyl, t-butyl, or chloroethyl.

3. A method according to claim 2, wherein $R_1$, $R_2$ and $R_3$ of the general formula (I) are all methyl group.

4. A method according to claim 2, wherein $R_1$, $R_2$ and $R_3$ of the general formula (I) are all chlorine atom.

5. A method according to claim 2, wherein $R_1$ is methyl group; and $R_2$ and $R_3$ are chlorine atom in the general formula (I).

6. A method according to claim 2, wherein $R_1$ and $R_2$ are methyl group; and $R_3$ is chlorine atom in the general formula (I).

7. A method according to claim 2, wherein R of the general formula (II) is hydrogen.

8. A method according to claim 2, wherein R of the general formula (II) is propyl group.

9. A method according to claim 2, wherein R of the general formula (II) is n-butyl group.

10. A method according to claim 2, wherein R of the general formula (II) is t-butyl group.

11. A method according to claim 2, wherein R of the general formula (II) is chloroethyl group.

12. A method according to claim 2, wherein 1-3 times of RCl of the general formula (II) is added to each mole of chloromethylsilane of the general formula (I).

13. A method according to claim 2, wherein RCl of the general formula (II) is 1:1 mixture of butyl chloride and hydrogen chloride.

14. A method according to claim 2, wherein the reaction is carried out in a stirred bed reactor equipped with a spiral band agitator or fluidized bed reactor.

15. A method according to claim 2, wherein the pressure of reactor is 1-5 atmospheric pressure.

16. A method according to claim 2, wherein about 1-50% of microspherical acid clay based on the amount of silicon is added during the reaction.

17. A method according to claim 2, wherein about 1-20% of copper or cuprous chloride based on the amount of silicon is added.

18. A method according to claim 2, wherein about 0.1-5% of calcium, barium, zinc, tin, cadmium, manganese, magnesium, silver, chromium, based on the amount of silicon is added as a promotor.

* * * * *